United States Patent [19]

Bayod Jasanda et al.

[11] Patent Number: 5,869,629
[45] Date of Patent: Feb. 9, 1999

US005869629A

[54] SYNTHESIS OF 9-DEOXO-9A-AZA-11,12-DEOXY-9A-METHYL-9A-HOMOERYTHROMYCIN A 11,12 HYDROGENORTHOBORATE DIHYDRATE AND A PROCESS FOR THE PREPARATION OF AZITROMICIN DIHYDRATE

[75] Inventors: D. Miguel Santos Bayod Jasanda; D. José Ramon Fernandez Gonzalez, both of Llanera, Spain

[73] Assignee: Asturpharma, S.A., Madrid, Spain

[21] Appl. No.: 890,771

[22] Filed: Jul. 11, 1997

[30] Foreign Application Priority Data

Jul. 11, 1996 [ES] Spain ................................. 9601561

[51] Int. Cl.$^6$ .................................................... C07H 17/08
[52] U.S. Cl. .............................. 536/7.2; 536/7.1; 536/7.3; 536/7.4; 536/7.5
[58] Field of Search ................................. 536/7.1, 7.2, 7.3, 536/7.4, 7.5; 424/180

[56] References Cited

U.S. PATENT DOCUMENTS 4,328,324  5/1982  Kock et al. .
4,328,334  5/1982  Kobrehel et al. .
4,517,359  5/1985  Kobrehel et al. .

*Primary Examiner*—James O. Wilson
*Attorney, Agent, or Firm*—Michaelson & Wallace; Peter L. Michaelson; Edward M. Fink

[57] ABSTRACT

The preparation of azitromycin dihydrate from 9-deoxo-9*a*-aza-11,12-deoxy-9*a*-methyl-9*a*-homoerythromycin A 11,12-hydrogenorthoborate, obtained by a step by step process starting from 9-deoxo-6-deoxy-6,9-epoxy-9,9*a*-dihydro-9*a*-azahomoerythromycin A is a process which takes place under mild conditions and with good yields.

7 Claims, 2 Drawing Sheets

SYNTHESIS OF 9-DEOXO-9A-AZA-11,12-DEOXY-9A-METHYL-9A-HOMOERYTHROMYCIN A 11,12 HYDROGENORTHOBORATE DIHYDRATE AND A PROCESS FOR THE PREPARATION OF AZITROMICIN DIHYDRATE

BACKGROUND OF THE INVENTION

1. Field of the Invention

Azitromycin is the USAN generic name of the product 9-deoxo-9a-aza-9a-methyl-9a-homoerythromycin A, which constitutes the first example of a new class of antibiotics (azalides) and is an effective therapeutic agent in the treatment of sexually transmitted diseases, infections of the respiratory apparatus and infections of the skin (H. A. Kirst, G. D. Sides, *Antimicrob. Agents Chemother*, 1989, 33, 1419–1422).

2. Description of the Prior Art

FIG. 1 shows the bibliographical background in relation to the synthesis of this macrolide. Azitromycin was first described by S. Djokic and G. Kobrehel in the Belgian Pat. No. 892,357 and in its related U.S. Pat. No. 4,517,359, obtained by means of the reductive alkylation of 9-deoxo-9a-aza-9a-homoerythromycin A (3), by treatment of said amine with a mixture of formic acid and aqueous formaldehyde under chloroform reflux, following the classical experimental conditions of the Eschweller-Clarke reaction.

The synthesis of 9-deoxo-9a-aza-9a-homoerythromycin A (3), is described by S. Djokic and G. Kobrehel in U.S. Pat. No. 4,328,334, and in the *J. Chem. Soc. Perkin Trans I*, 1986, 1881. In these publications, the product is found denominated as 10-dihydro-10-deoxo-11-azaerythromycin A, and it is obtained by a synthetic sequence which schematically consists of: Obtaining the oxime of erythromycin A (1) by reaction of erythromycin A hydroxylamine hydrochloride. Obtaining the iminoether 9-deoxo-6-deoxy-6,9-epoxy-9,9a-dihydro-9a-azahomoerythromycin A (2) by a transposition of the oxime of erythromycin A (1). This iminoether and the process for obtaining it is also described in Pat. WO 94/26758 and in Eur. Pat. 0,137,132. In U.S. Pat. No. 4,328,324 this iminoether is erroneously assigned the structure of the lactam obtained by a Beckman transposition starting from the oxime of erythromycin. Obtaining 9-deoxo-9a-aza-9a-homoerythromycin A (3) by reduction of the iminoether (2) with sodium borohydride in methanol, or by catalytic hydrogenation in the presence of platinum dioxide with acetic acid as a solvent.

In the literature previously mentioned, the reduction of the iminoether 9-deoxo-6-deoxy-6,9-epoxy-9,9a-dihydro-9a-azahomoerythromycin A (2) can be carried out by following two different methods:

a) Reduction with sodium borohydride in methanol at 0° C. This method presents a number of drawbacks: methanol destroys the reducing agent, and some of the steps which include the isolation of the reaction product (azaerythromycin) affect the quality of the same. The literature previously cited describes how, in the presence of acid aqueous media, azaerythromycin (3) becomes partially hydrolysed to yield deosaminylazaerythromycin (6) (S. Djokic et al. in *J. Chem. Soc. Perkin Trans I*, 1986, 1881).

b) Catalytic hydrogenation with platinum dioxide, at high pressures (70 atm). The drawbacks of this method, from the point of view of its industrial application are obvious: the high working pressures and the manipulation of platinum dioxide.

The Eschweiler-Clarke reaction employed in U.S. Pat. No. 4,517,359 and in the *J. Chem. Res.*, 1988, 132; and *idem miniprint.*, 1988, 1239, for preparing azitromycin (4) results in the formation of some reaction impurities such as the case of the formamide derived from the amine 9-deoxo-9a-aza-9a-homoerythromycin A.

The structural elucidation studies of azitromycin (4) (S. Djokic and G. Kobrehel *J. Chem. Res.*, 1988, 132; and *idem miniprint.*, 1988, 1239) have demonstrated its existence in two crystalline forms: hygroscopic monohydrate (4) and non-hygroscopic crystalline dihydrate (5). The latter is the preferred form for its manipulation with the object of producing formulations of therapeutic use, as described in the Eur. Pat. No. 0,298,650.

STATEMENT OF THE INVENTION

The object of the present invention is depicted in FIG. 2, which describes the preparation, in four steps, of 9-deoxo-9a-aza-9a-methyl-9a-homoerythromycin A, azitromycin dihydrate (5), starting from the iminoether 9-deoxo-6-deoxy-6,9-epoxy-9,9a-dihydro-9a-azahomoerythromycin A (2). The process herein described involves the preparation of two new products which are used as intermediates in the synthesis of azitromycin: 9-deoxo-9a-aza-11,12-deoxy-9a-homoerythromycin A 11,12-hydrogenorthoborate (8) and 9-deoxo-9a-aza-11,12-deoxy-9a-methyl-9a-homoerythromycin A 11,12-hydrogenorthoborate (9). It is also an object of the present invention to convert the hygroscopic form of azitromycin (4) into its non-hygroscopic dihydrate form (5), by means of agitation of the hygroscopic form in an acetone-water mixture with seeding of crystals of the dihydrate form.

DETAILED DESCRIPTION OF THE INVENTION

Figure 1:
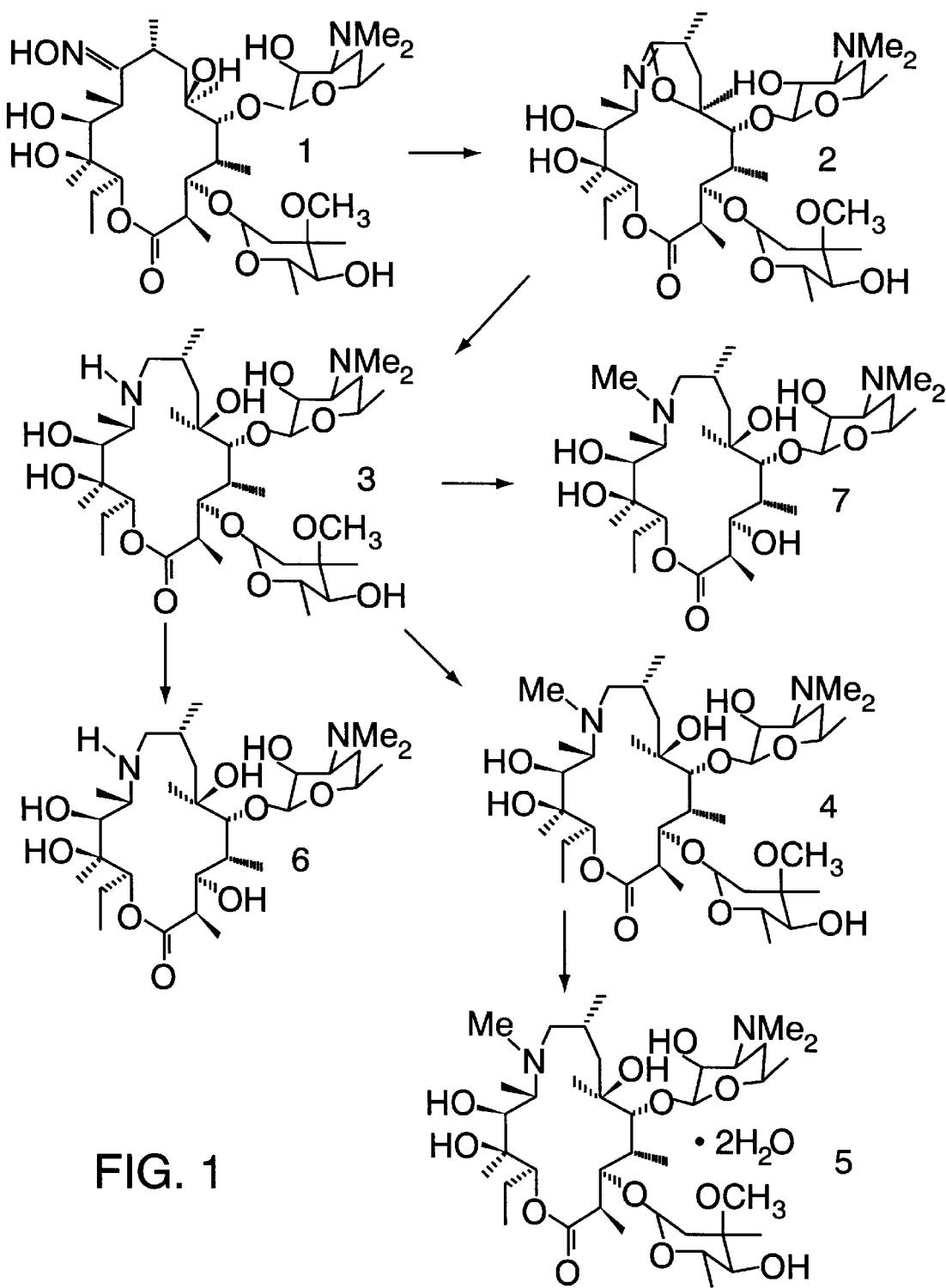
Figure 2:
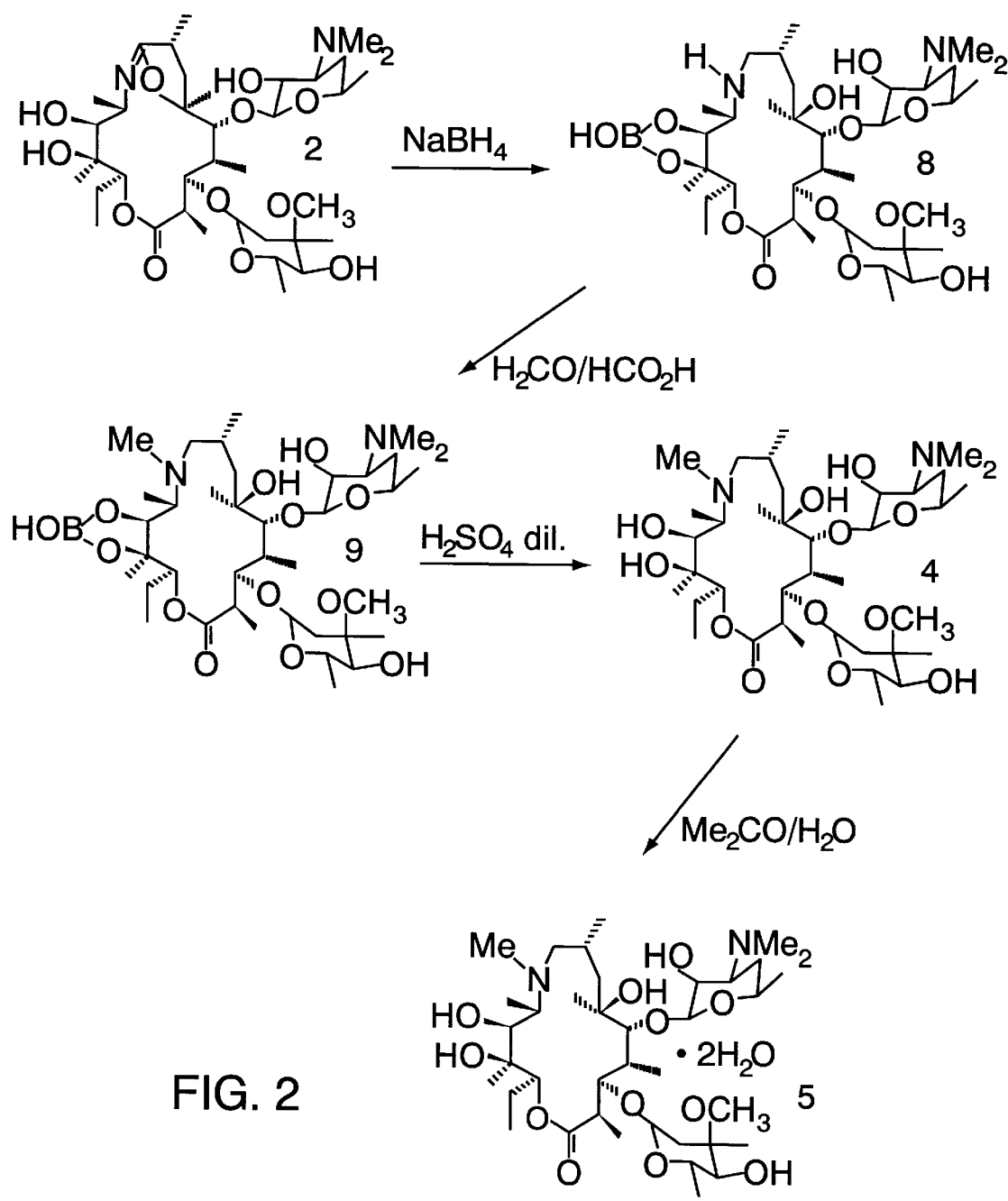

The design of the new process for the synthesis of azitromycin which is the object of the present invention originates from careful comparison of the product obtained and of the set of impurities present in different batches of azitromycin obtained at the laboratory scale by repetition of the experimental conditions described by the discoverers of the product (S. Djokic et al.) in *J. Chem. Soc. Perkin Trans I*, 1986, 1881, *J. Chem. Res.*, 1988, 132; and *idem miniprint.*, 1988, 1239.

The various batches studied differentiate from one another in the form of obtaining the azaerythromycin mentioned from the iminoether 9-deoxo-6-deoxy-6,9-epoxy-9,9a-dihydro-9a-azahomoerythromycin A (2): either by reduction with sodium borohydride or by catalytic hydrogenation.

These studies have allowed us to make the following original observations:

The reduction of the iminoether 9-deoxo-6-deoxy-6,9-epoxy-9,9a-dihydro-9a-azahomoerythromycin A (2) by catalytic hydrogenation is possible in the presence of platinum over activated carbon as a catalyst. The method described in the present invention for the reduction of 9-deoxo-6-deoxy-6,9-epoxy-9,9a-dihydro-9a-azahomoerythromycin A (2) describes its catalytic hydrogenation at low pressures (between 3 and 10 atm) in the presence of platinum over activated carbon as a catalyst, and by using aqueous acid systems: methanol/water/hydrochloric or aqueous 2N acetic acid, as solvent. Reduction times are moderate (12–16 hours), and the experimental work of isolating 9-deoxo-9a-aza-9a-homoerythromycin A (3) is simple and does not affect its stability: simple filtration of the catalyst, and subsequent extraction in an alkaline medium, concentration and precipitation.

In the study of the contaminants present in the 9-deoxo-9a-aza-9a-homoerythromycin A (3) (azaerythromycin) obtained by reduction with sodium borohydride, the presence of a contaminant which has not been described in the literature, 9-deoxo-9a-aza-11,12-deoxy-9a-homoerythromycin A 11,12-hydrogenorthoborate (8), has been observed.

In the study of the contaminants present in 9-deoxo-9a-aza-9a-methyl-9a-homoerythromycin A (azitromycin) (4), prepared from azaerythromycin obtained by reduction with sodium borohydride, the presence of a contaminant which has not been described in the literature, 9-deoxo-9a-aza-11,12-deoxy-9a-methyl-9a-homoerythromycin A 11,12-hydrogenorthoborate (9), has been observed.

The formation of these 11,12-hydrogenorthoborates must not surprise anybody, since, as it is well known, the formation of this functional group is one of the classic methods protecting neighboring diols ("*Protective Groups in Organic Synthesis*", T. W. Greene, Wyley & Sons, 2nd, p 115, 141, and 173; R. J. Ferrier, *Adv. Carbohydr. Chem. Biochem.*; 35, 31–80, 1978).

The presence of boron in compounds (8) and (9) was demonstrated by $^{11}$B-NMR and mass spectroscopy. For its structural elucidation, one has resorted to special NMR techniques such as heteronuclear bidimensional correlations: HMAC and HMBC. It is possible to state that the OH groups which occupy positions 11 and 12 in the macrolide, bind to the boron atom, as can be deduced from the deovershading which said carbon atoms present.

|  | Product | | | |
| --- | --- | --- | --- | --- |
|  | 3 | 4 | 8 | 9 |
| $C_{11}$ | 71,94 | 72,32 | 79,63 | 79,40 |
| $C_{12}$ | 72,63 | 73,08 | 76,46 | 77,09 |

Solvent: $CDCl_3$
T° = 293° K.
v of $^1H$ = 400 MHz; v of $^{13}C$ = 100,61 MHz.

The process for the synthesis of 9-deoxo-9a-aza-9a-methyl-9a-homoerythromycin A (azitromycin) (4) which is the object of the present invention comprises using the 11,12-hydrogenorthoborates (8) and (9) as intermediates in the synthesis, adequately modifying the reaction conditions so as to make them be the intermediate products obtained. The substantial difference of this synthetic method is that by carrying out the hydrolysis of 9-deoxo-9a-aza-11,12-deoxy-9a-methyl-9a-homoerythromycin A 11,12-hydrogenorthoborate (9), in the conditions described in the experimental part, the presence of both deosaminyiazaerythromycin (6) and deosaminylazitromycin (7) (acid degradation products), as well as the presence of the hydrogenorthoborates themselves (8) and (9), is minimized, all of them being contaminants in the synthesis of azitromycin (4). The concentration of 9-deoxo-9a-aza-11,12-deoxy-9a-methyl-9a-homoerythromycin A 11,12-hydrogenorthoborate (9) as a contaminant is a determinant factor in the conversion of hygroscopic azitromycin (4) into azitromycin dihydrate (5).

In this way, the product which is the object of this invention is obtained by a process which comprises the following steps:

The first step is the reduction of the iminoether 9-deoxo-6-deoxy-6,9-epoxy-9,9a-dihydro-9a-azahomoerythromycin A (2) with sodium borohydride in methanol at between −10° and 0° C. The experimental work of the process is carried out in an aqueous medium, but in the absence of mineral acid, which leads to the formation of 9-deoxo-9a-aza-11,12-deoxy-9a-homoerythromycin A 11,12-hydrogenorthoborate (8).

The second step involves the reductive alkylation of 9-deoxo-9a-aza-11,12-deoxy-9a-homoerythromycin A 11,12-hydrogenorthoborate (8) with formaldehyde and formic acid under reflux with an organic solvent (preferably chloroform or acetonitrile). In this manner 9-deoxo-9a-aza-11,12-deoxy-9a-methyl-9a-homoerythromycin A 11,12-hydrogenorthoborate (9) is obtained.

The third step is the hydrolysis, in an organic medium (preferably acetonitrile) and in the presence of dilute mineral acid (preferably sulphuric acid), of 9-deoxo-9a-aza-11,12-deoxy-9a-methyl-9a-homoerythromycin A 11,12-hydrogenorthoborate (9), to yield azitromycin in its hygroscopic form (4).

The fourth step is the recrystallization of hygroscopic azitromycin from a mixture acetone and water to yield 9-deoxo-9a-aza-9a-methyl-9a-homoerythromycin A dehydrate (azitromycin dihydrate) (5).

Azitromycin dihydrate is easily distinguishable from hygroscopic azitromycin by means of the following differentiative assays:

a) The dehydrate form keeps its percentile water content constant at values (4,5–5%) which are very close to the theoretical value (4,6%).

b) Thermogravimetric analysis (TGA) of azitromycin dihydrate indicates a total weight loss of between 4,5 and 5% at 200° C., yielding a plot with no inflections throughout the whole process.

c) The differential calorimetry analysis (DSC) of azitromycin dehydrate reveals the presence of a single endotherm which may vary between 126° and 135° C., with an energy absorbed during the process which ranges between 27 and 34 cal/g.

d) The infrared spectra in KBr of both crystalline forms presents clear differences:

| azitromycin dihydrate v $(cm^{-1})$ | hygroscopic azitromycin v $(cm^{-1})$ |
| --- | --- |
| 3500 and 3600, 2 sharp bands | 3500, 1 wide band |
| 1340 | does not present any |
| 1270 and 1285, 2 sharp bands | 1280, 1 wide band |
| 1080 | does not present any |

EXPERIMENTAL PART

Preparation of 9-deoxo-9a-aza-9a-homoerythromycin A.

2 g of the iminoether 9-deoxo-6-deoxy-6,9-epoxy-9,9a-dihydro-9a-aza-homoerythromycin A are dissolved in a solution of 4.8 ml of acetic acid in 40 ml $H_2O$, and 2 g of platinum over 5% activated carbon are added (with a 60% $H_2O$ content), and hydrogenation is begun at a pressure of 75 psi. After 12 hours reaction the catalyst is filtered and the liquid phase is transferred to 100 ml of methylene chloride and 100 ml $H_2O$, the aqueous phase is adjusted to pH=9 and the organic phase is decanted. The aqueous phase is extracted with 2×50 ml methylene chloride, the organic phases are pooled, dried with anhydrous sodium sulphate and evaporated to yield 1,55 g of 9-deoxo-9a-aza-9a-homoerythromycin A.

| IR (KBr) | $V_{max}$ = 3500, 2980, 2960, 1740, 1470, 1380, 1180, 970 cm$^{-1}$ |
|---|---|
| $^1$H-NMR (CDCl$_3$) (partial) | δ = 2,3 (NMe$_2$), 3,35 (OMe), ppm |
| $^{13}$C-NMR (CDCl$_3$) (partial) | δ = 178,9 (C = O), 72,63 C$_{12}$), 71,94 (C$_{11}$), 57,3 (C$_9$), 56,9 (C$_{10}$), 49,4 (OMe), 40,2 (NMe$_2$) ppm |
| HPLC | Corresponds according to USP XXIII |
| TLC | rf = 0,54 (petroleum ether:ethyl acetate:diethylamine 75:25:10; developer: ethanol/vanillin (sulphuric acid) |

Preparation of 9-deoxo-9a-aza-11,12-deoxy-9a-homoerythromycin A 11,12-hydrogenorthoborate.

89 g of 9-deoxo-6-deoxy-6,9-epoxy-9,9a-dihydro-9a-aza-homoerythromycin A are dissolved in 450 ml of methanol and are cooled to between −5° and −10° C. While keeping the temperatures in the interval specified, 16 portions of 2.2 g each of sodium borohydride are added. Temperature and agitation conditions are maintained for 2 additional hours and the bulk of the reaction is allowed to reach 20° C. After 20 h the methanol is evaporated to dryness. The residue is dissolved in 500 ml of methylene chloride and 750 ml of water, shaking for 30 min. The organic phase is separated and the aqueous phase is extracted with 250 ml methylene chloride. The organic phases are pooled, filtered over celite, dried over anhydrous sodium sulphate and concentrated to dryness to yield 85 g of 9-deoxo-9a-aza-11,12-deoxy-9a-homoerythromycin A 11,12-hydrogenorthoborate.

| IR (KBr) | $V_{max}$ = 3500, 2980, 2960, 1730, 1470, 1390, 1170, 1090, 1060 cm$^{-1}$ |
|---|---|
| $^1$H-NMR (CDCl$_3$) (partial) | δ = 2,21 (NMe$_2$), 3,27 (OMe), ppm |
| $^{13}$C-NMR (CDCl$_3$) (partial) | δ = 180,0 (C = O), 79,63 C$_{11}$), 76,46 (C$_{12}$), 58,7 (C$_{10}$), 57,1 (C$_9$), 49,4 (OMe), 40,2 (NMe$_2$) ppm |
| $^{11}$B-NMR (CDCl$_3$) | δ = 9,9 ppm ω$_{1/2}$ = 200 Hz |
| TLC | rf = 0,28 (petroleum ether:ethyl acetate:diethylamine 75:25:10; developer: ethanol/vanillin (sulphuric acid) |

Preparation of 9-deoxo-9a-aza-11,12-deoxy-9a-methyl-9a-homoerythromycin A 11,12-hydrogenorthoborate.

50 g of 9-deoxo-9a-aza-11, 12-deoxy-9a-homoerythromycin A 11,12-hydrogenorthoborate are dissolved in 500 ml of chloroform, and subsequently a mixture of 5,5 ml formic acid and 11,75 ml aqueous 35–40% formaldehyde is added. The reaction mixture is heated under reflux for 14 h and is subsequently cooled down to 15°–20° C. 500 ml of water are added and the mixture is taken to pH=4 by adding 20% sulphuric acid. The mixture is shaken for 15 min and the organic phase is separated and discarded. 350 ml of methylene chloride are added to the acid aqueous phase, and 48% lime is added to take said aqueous phase to pH=9. The mixture is shaken for 15 min and the lower organic layer is separated. The alkaline aqueous phase is extracted with 2×100 ml methylene chloride. The organic phases are pooled and filtered over celite, dried over anhydrous sodium sulphate and evaporated to dryness. The residue obtained is washed twice with 250 ml ethyl ether, thus obtaining a dry residue of 29 g of 9-deoxo-9a-aza-11, 12-deoxy-9a-methyl-9a-homoerythromycin A 11,12-hydrogenorthoborate.

| IR (KBr) | $V_{max}$ = 3500, 1730, 1470, 1390, 1090, 1070 cm$^{-1}$ |
|---|---|
| $^1$H-NMR (CDCl$_3$) (partial) | δ = 2,00 (NMe$_2$), 2,30 (NMe), 3,37 (OMe), ppm |
| $^{13}$C-NMR (CDCl$_3$) (partial) | δ = 179,9 (C = O), 79,40 C$_{11}$), 77,09 (C$_{12}$), 68,84 (C$_9$), 64,08 (C$_{10}$), 49,36 (OMe), 40,18 (NMe$_2$), 34,39 (NMe) ppm |
| $^{11}$B-NMR (CDCl$_3$) | δ = 10,1 ppm ω$_{1/2}$ = 180 Hz |
| m/e | M$^+$ = 775,5 |
| TLC | rf = 0,38 (petroleum ether:ethyl acetate:diethylamine 75:25:10; developer: ethanol/vanillin (sulphuric acid) |

Hydrolysis of 9-deoxo-9a-aza-11,12-deoxy-9a-methyl-9a-homoerythromycin A 11,12-hydrogenorthoborate.
Synthesis of 9-deoxo-9a-aza-9a-methyl-9a-homoerythromycin A (Azitromycin).

22 g of 9-deoxo-9a-aza-11,12-deoxy-9a-methyl-9a-homoerythromycin A 11,12-hydrogenorthoborate are dissolved in 250 ml acetonitrile to which 125 ml of water are subsequently added. 20% sulphuric acid is added to the mixture to take it to pH=2, and agitation is maintained for 30 min. The acid solution is poured into a mixture of 350 ml of methylene chloride and 350 ml of water, immediately adding 48% lime until the pH of the aqueous phase is adjusted to 9. The mixture is shaken for 15 min and the lower organic phase is separated. The alkaline aqueous phase is extracted with 2×100 ml methylene chloride. The methylene chloride is pooled, filtered over celite and evaporated to dryness. The residue is dissolved in 50 ml ethanol and 60 ml of water are added to it over 30 min. Precipitation is allowed to occur for 2 h, and the mixture is then filtered and vacuum-dried at 40° C. to yield 15 g of 9-deoxo-9a-aza-9a-methyl-9a-homoerythromycin A (Azitromycin).

| IR (KBr) | $V_{max}$ = 3500, 3000, 2970, 1740, 1470, 1380, 1280, 1060 cm$^{-1}$ |
|---|---|
| $^1$H-NMR (CDCl$_3$) (partial) | δ = 2,31 (NMe$_2$), 2,34 (NMe), 3,38 (OMe), ppm |
| $^{13}$C-NMR (CDCl$_3$) (partial) | δ = 178,9 (C = O), 78,03 C$_{12}$), 72,32 (C$_{11}$), 69,88 (C$_9$), 62,13 (C$_{10}$), 49,37 (OMe), 40,23 (NMe$_2$), 35,92 (NMe) ppm |
| $^{11}$B-NMR (CDCl$_3$) | δ = 9,9 ppm ω$_{1/2}$ = 200 Hz |
| m/e | M$^+$ = 749,5 |
| HPLC | corresponds according to USP XXIII |
| TLC | rf = 0,62 (petroleum ether:ethyl acetate:diethylamine 75:25:10; developer: ethanol/vanillin (sulphuric acid) |

Preparation of 9-deoxo-9a-aza-9a-methyl-9a-homoerythromycin A dihydrate.

51 g of hygroscopic azitromycin are dissolved in 130 ml acetone and the solution is filtered. 100 ml of water are added over 30 minutes, and the solution is stirred at room temperature for 24 h. The precipitated solid is filtered and vacuum-dried at 40° C. to yield 45 g of 9-deoxo-9a-aza-9a-methyl-9a-homoerythromycin A dihydrate. From the point of view of their spectroscopic data, the hygroscopic and dihydrate forms only differ in some bands of their infrared spectra.

| IR (KBr) | $V_{max}$ = 3600, 3520, 3000, 2970, 1740, 1470, 1380, 1340, 1285, 1270, 1080, 1060 cm$^{-1}$ |
|---|---|

Conversion of hygroscopic azitromycin into azitromycin dihydrate.

A mixture of 35 ml acetone and 27 ml of water is prepared, and 14 g of azitromycin dihydrate are added to it. 3.5 g of azitromycin dihydrate are added and the suspension is shaken at room temperature for 24 h. It is then filtered and vacuum-dried at 40° C. to yield 13,6 g of azitromycin dihydrate.

We claim:

1. The product 9-deoxo-9a-aza-11,12-deoxy-9a-methyl-9a-homoerythromycin A 11,12-hydrogenorthoborate.

2. A process for the preparation of 9-deoxo-9a-aza-9a-methyl-9a-homoerythromycin A (Azitromycin) in its dihydrate form, characterized by the recrystallization of the hygroscopic form of azitromycin in an acetone-water mixture.

3. A process for the preparation of 9-deoxo-9a-aza-9a-methyl-9a-homoerythromycin A (Azitromycin) in its dihydrate form, characterized by the agitation of crystals of the hygroscopic form of azitromycin in an acetone-water mixture, with an initial addition of crystals of the dihydrate form.

4. A process for the preparation of 9-deoxo-9a-aza-9a-methyl-9a-homoerythromycin A (Azitromycin) characterized by the hydrolysis of 9-deoxo-9a-aza-11,12-deoxy-9a-methyl-9a-homoerythromycin A 11,12-hydrogenorthoborate in an organic solvent by the action of a dilute mineral acid at room temperature and at a pH range comprised between 2 and 4.

5. A process for the preparation of 9-deoxo-9a-aza-11,12-deoxy-9a-methyl-9a-homoerythromycin A 11,12-hydrogenorthoborate characterized by the reaction of 9-deoxo-9a-aza-11,12-deoxy-9a-homoerythromycin A 11,12-hydrogenorthoborate with formic acid and aqueous formaldehyde under reflux with an organic solvent.

6. A process for the preparation of 9-deoxo-9a-aza-11,12-deoxy-9a-homoerythromycin A 11,12-hydrogenorthoborate characterized by the reduction of 9-deoxo-6-deoxy-6,9-epoxy-9,9a-dihydro-9a-aza-homoerythromycin A with sodium borohydride in methanol as solvent, at a temperature ranging from $-10°$ and $0°$ C. followed by subsequent hydrolysis in the absence of the acid mineral medium.

7. A process for the obtention of 9-deoxo-9a-aza-9a-homoerythromycin A characterized by the catalytic hydrogenation at a pressure ranging from 3 to 10 atm) of 9-deoxo-6-deoxy-6,9-epoxy-9,9a-dihydro-9a-azahomoerythromycin A, using Platinum over carbon as a catalyst and using a mixture of alcohol and aqueous acid as solvent.

* * * * *